(12) United States Patent
Zardini

(10) Patent No.: US 9,592,311 B2
(45) Date of Patent: Mar. 14, 2017

(54) WASHING MACHINE AND CORRESPONDING WASHING METHOD

(75) Inventor: Fabio Zardini, Castelfranco Veneto (IT)

(73) Assignee: STEELCO SPA, Riese Pio X (IT)

( * ) Notice: Subject to any disclaimer, the term of this patent is extended or adjusted under 35 U.S.C. 154(b) by 791 days.

(21) Appl. No.: 13/413,425

(22) Filed: Mar. 6, 2012

(65) Prior Publication Data
US 2012/0227767 A1 Sep. 13, 2012

(30) Foreign Application Priority Data
Mar. 7, 2011 (IT) .............................. UD2011A0029

(51) Int. Cl.
*B08B 3/02* (2006.01)
*A61L 2/04* (2006.01)

(52) U.S. Cl.
CPC ............. *A61L 2/04* (2013.01); *A61L 2202/17* (2013.01); *A61L 2202/24* (2013.01)

(58) Field of Classification Search
CPC ..... A61L 2202/17; A61B 1/123; A61B 1/125; A61B 1/128; A47L 15/0015; A47L 15/4285; A47L 15/4291; A47L 15/4219; A47L 15/4214; Y02B 40/44; Y02B 50/44; Y02B 40/54; Y02B 40/05; B08B 3/02
USPC ........................................................ 134/108
See application file for complete search history.

(56) References Cited

U.S. PATENT DOCUMENTS

| | | | | |
|---|---|---|---|---|
| 1,559,727 A | * | 11/1925 | Merseles et al. | .......... 134/103.1 |
| 2,621,666 A | * | 12/1952 | Hiort af Ornas | ... A47L 15/0023 |
| | | | | 134/107 |
| 3,709,732 A | * | 1/1973 | Thomen | ...................... 134/57 D |
| 4,226,642 A | | 10/1980 | Baran | |
| 4,277,290 A | * | 7/1981 | Andrews et al. | ................ 134/10 |
| 4,326,552 A | * | 4/1982 | Bleckmann | ......... A47L 15/4285 |
| | | | | 134/102.3 |
| 5,829,459 A | * | 11/1998 | Milocco | .............. A47L 15/4291 |
| | | | | 134/201 |
| 2003/0190256 A1 | * | 10/2003 | Halstead et al. | ................ 422/28 |
| 2006/0037632 A1 | | 2/2006 | Nito et al. | |

(Continued)

FOREIGN PATENT DOCUMENTS

| | | | | |
|---|---|---|---|---|
| CH | EP 1864603 A2 | * | 12/2007 | ......... A47L 15/4231 |
| DE | 3901169 A1 | * | 7/1990 | ......... A47L 15/0047 |

(Continued)

OTHER PUBLICATIONS

FR2790688—Machine Translation, Sep. 2000.*

(Continued)

*Primary Examiner* — Michael Kornakov
*Assistant Examiner* — Marc Lorenzi
(74) *Attorney, Agent, or Firm* — Vorys, Sater, Seymour and Pease LLP

(57) ABSTRACT

A washing machine suitable to effect a washing treatment, thermo-disinfection and possible drying of objects, including a washing chamber in which the objects to be treated are disposed, and a washing circuit including a plurality of exit paths for a washing liquid to be distributed toward the objects to be treated. On the bottom of the washing chamber, in association with a corresponding discharge aperture, valve means to discharge the washing liquid are disposed, which are directly connected to a pipe that discharges directly into the sewerage system.

18 Claims, 2 Drawing Sheets

(56) References Cited

U.S. PATENT DOCUMENTS

| | | | |
|---|---|---|---|
| 2006/0237052 A1* | 10/2006 | Picardat et al. | ............ 134/56 D |
| 2008/0041419 A1* | 2/2008 | Gaus | ....................... A47L 15/24 |
| | | | 134/10 |
| 2008/0282750 A1 | 11/2008 | Yang et al. | |
| 2009/0050181 A1* | 2/2009 | Johansson | ....................... 134/34 |
| 2011/0048459 A1* | 3/2011 | Hesterberg | .......... A47L 15/0023 |
| | | | 134/18 |
| 2011/0083699 A1* | 4/2011 | Rosenbauer | ........ A47L 15/0002 |
| | | | 134/18 |
| 2011/0114140 A1* | 5/2011 | Heisele | ............... A47L 15/0015 |
| | | | 134/56 D |

FOREIGN PATENT DOCUMENTS

| | | | | |
|---|---|---|---|---|
| DE | 102008030537 | * | 12/2009 | ......... A47L 15/0002 |
| EP | 0016889 A1 | | 10/1980 | |
| EP | 1992730 A1 | | 11/2008 | |
| FR | 2790688 A1 | * | 9/2000 | ............... B08B 3/04 |
| WO | WO 2005055798 A1 | * | 6/2005 | ............. A47L 15/24 |
| WO | 2005083168 A1 | | 9/2005 | |
| WO | WO 2006037447 A1 | * | 4/2006 | ............. A47L 15/00 |

OTHER PUBLICATIONS

WO2006037447—Machine Translation, Apr. 2006.*
DE3901169—Machine Translation, Jul. 1990.*
EP1864603—Machine Translation, Dec. 2007.*
WO2005055798—Machine Translation, Jun. 2005.*
EP Search Report from IT Appl No. UD20110029 dated Sep. 6, 2011.

\* cited by examiner

WASHING MACHINE AND CORRESPONDING WASHING METHOD

CROSS-REFERENCE TO RELATED APPLICATIONS

This claims the benefit of Italian Patent Application No. UD2011A000029, filed on 7 Mar. 2011.

FIELD OF THE INVENTION

The present invention concerns a washing machine to perform treatments of washing, thermo-disinfection and possibly drying, of objects, such as for example objects used in the health sector which, once washed, can be re-used, for example instruments used in operating rooms, laboratories and suchlike.

BACKGROUND OF THE INVENTION

It is known to make a washing machine for objects that comprises a washing chamber in which the objects to be washed are disposed, one or more tanks of chemical detergents and an inlet path for the liquid, generally water, which is mixed with the chemical detergents.

A hydraulic circuit is provided in the washing chamber, with nozzles suitable to distribute the washing liquid toward the objects. The chamber is hydraulically connected, by means of a discharge valve, with an outlet tank located on the bottom; the outlet tank is in turn directly connected with a sewerage system, suitable to receive the discharged washing liquid.

One disadvantage of the known machine is that the discharge capacity of the discharge valve used makes it necessary to have the outlet tank functioning as a store for the washing liquid to be discharged, so as to adapt to possible limited capacities of the sewerage system.

Another disadvantage of the known washing machine is the great waste at least of washing liquid, due to its being discharged directly into the sewerage system.

Document WO-A-20005/083168 describes a washing machine for textile articles of a known type, which comprises a double washing chamber, of which a rotary internal chamber and a fixed external chamber, and a washing circuit to distribute a washing liquid with a lipophilic base on the textile articles to be treated in the washing chamber. On the bottom of the external chamber there is an exit pipe for the washing liquid, downstream of which the following are disposed in series: a three-way valve, a pump with a maximum delivery rate of 11.356 liters (3 gallons) per minute, a filter and a recovery tank that accumulates a certain quantity of liquid to separate the fluids by means of gravity and difference in density between them, and which provides a sensor for the level of the volume of liquid in the tank to determine when to start emptying the tank. Downstream of the recovery tank there is a pump with a maximum delivery rate of 2.8 liters per minute which leads to a two-way valve, which in a first position allows to discharge into the sewerage network, or into a dedicated container, and in a second position connects the outlet of the pump with a system to recover the fluids.

One purpose of the present invention is to obtain a washing machine which is simple and economical to construct, which is not bulky and whose effectiveness is independent of the sewerage network to which it is hydraulically connected.

Another purpose is to obtain savings in the use of the quantity of water and consequently of the chemical detergents, reducing the economic and environmental impact thereof.

Another purpose is to obtain a washing machine which has good energy efficiency, allowing to recover at least part of the heat used in the various steps of the washing cycle.

Another purpose is to obtain a machine that performs a complete washing cycle in the shortest possible time, preheating the necessary fluids and shortening the filling and discharge times.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purposes, a washing machine according to the present invention is used to carry out a washing, thermo-disinfection and possible drying treatment for objects, and comprises a washing chamber in which the objects to be treated are disposed, a washing circuit comprising a plurality of exit paths for a washing liquid, generally water, to be distributed to the objects to be treated.

According to the present invention, the washing chamber comprises a bottom which has a corresponding discharge aperture on which, at exit, a single valve for the rapid discharge of the washing liquid is directly mounted; the exit of the valve is connected in direct communication to the inlet of a pipe that discharges directly into the sewerage system, provided for this purpose, without providing, between the rapid discharge valve and the pipe that discharges into the sewerage system, any other intermediate hydraulic members, pipes, accumulation or treatment tanks.

The present invention thus does not provide to use, nor does it need, an accumulation tank or store, for example to adapt to the capacities of the sewerage system downstream of discharge and is therefore less complex and bulky, and also more economical.

According to some forms of embodiment of the present invention, the rapid discharge valve has a cut-off plate, or other equivalent element with a cut-off function, with a shape mating to the discharge aperture and positioned mobile inside the bottom of the washing chamber between a first position in which it closes the discharge aperture and a second position in which it is distanced from the discharge aperture in order to allow the rapid passage of the washing liquid to be discharged.

According to some forms of embodiment of the present invention, the valve comprises rapid drive mechanical means configured to determine a rapid displacement of the cut-off plate between the first and second position and associated with actuator means directly connected to the rapid drive mechanical means.

In some forms of embodiment, the rapid drive mechanical means comprise a drive rod connected to the cut-off plate, which extends linearly from the plate toward the outside with respect to the discharge aperture and connected at the lower part to the actuator means. This linear mechanical configuration determines a rapid axial drive of the cut-off plate and hence an adequate discharge of the discharge liquid.

In other forms of embodiment, the rapid drive mechanical means comprise rocker arm means, which allow an equally rapid movement of the cut-off plate between the first and second position.

In some forms of embodiment, the machine comprises a plurality of tanks suitable to contain a washing liquid such as water, to be introduced selectively into the washing chamber and associated with heat exchange means, means to feed cold water or other pre-wash liquid inside the chamber, means to feed cold water or other pre-wash liquid, inside the chamber, means to feed one or more chemical detergent components inside the chamber and feed means associated with a first of the tanks, to feed water, such as de-mineralized water, or other liquid suitable for thermo-disinfection, inside the chamber.

In variant solutions, the cold water feed means are dedicated means that introduce the cold water directly into the washing chamber.

In other variant solutions, the cold water feed means are formed by one of the tanks containing the washing liquid.

According to some forms of embodiment, the heat exchange means of the first tank are configured to heat the liquid to a temperature suitable for thermo-disinfection.

In some forms of embodiment, the heat exchange means of a second of the tanks are configured to heat the liquid to a temperature comprised between about 55° C. and about 65° C.

Furthermore, in other forms of embodiment, the heat exchange means of a third of the tanks are configured to pre-heat the liquid fed by the feed means, recovering heat from the hot liquid accumulated in the third tank, with obvious advantages in terms of energy efficiency and hence reduction in costs.

Moreover, in some variants, the washing circuit comprises one or the third of the tanks, to receive and accumulate directly or indirectly a determinate quantity of hot washing liquid from the bottom of the chamber, and second re-circling means which connect the tank hydraulically inside the washing chamber and configured to transfer, by means of pumping means, the quantity or part of the quantity of hot washing liquid present in the tank, directly inside the washing chamber.

The third recovery and accumulation tank, for heat exchange and re-circling, can be made disposed in direct connection with the bottom of the washing chamber, or can be connected to the first re-circling means.

In some forms of embodiment, the washing machine comprises means to heat the washing liquid at entrance to the washing chamber to a desired temperature, normally between 75° C. and 95° C., or a lower temperature, for example between 55° C. and 70° C., if a chemical wash is to be carried out.

In some forms of embodiment of the present invention, the washing circuit comprises first re-circling means that develop from the bottom of the washing chamber toward the heating means and are thus suitable to transfer the washing liquid, by means of suitable pumping means, toward the heating means, from where, once they have been taken or returned to the desired temperature, they are again introduced into the washing chamber.

This solution also allows a considerable recovery of the enthalpy content of the washing liquid, and hence saving in the power needed to increase the heat energy of the washing liquid.

This solution allows a considerable saving at least of the washing liquid, especially considering that it is thus possible to re-use the liquid used in the final rinsing operation, which is normally practically clean and in any case is suitable to be used to start a new washing cycle of other objects.

In other forms of embodiment, the washing chamber comprises a drying circuit configured to blow in drying air at a determinate temperature inside the washing chamber, in order to dry the washed objects.

In some forms of embodiment of the present invention, the drying circuit is selectively connectable to the heating means of the washing liquid, which are thus advantageously used, on each occasion and according to the steps of the treatment cycle provided by the work program, to heat the washing liquid and also the drying air.

In some forms of embodiment of the present invention, the washing circuit and the drying circuit coincide, thus considerably simplifying the construction and management of the washing machine in question.

The present invention also concerns a method for carrying out a washing treatment, thermo-disinfection and possible drying of objects, which provides to dispose the objects to be treated in a washing chamber and to distribute a washing liquid toward the objects to be washed. The method provides to discharge the washing liquid from a discharge aperture of the bottom of the washing chamber through a single rapid discharge valve of the washing liquid mounted directly at exit from the discharge aperture into a pipe which has its entrance connected in direct communication with the exit of the rapid discharge valve, and hence without providing any intermediate hydraulic members, pipes, or tanks, and which discharges directly into the sewerage system.

In some forms of embodiment, the method according to the present invention provides to recover at least part of the heat energy of the liquid used in the thermo-disinfection so as to pre-heat one or more of the fluids used in the other steps of the treatment performed.

In other forms of embodiment, the method according to the present invention provides to re-use the liquid used in the thermo-disinfection directly in at least one of the other steps of the treatment performed.

In some forms of embodiment of the present invention, the method comprises a cold pre-wash step, a hot washing step between about 55° C. and about 65° C. with one or more chemical detergents, a hot rinsing step and a final rinsing and thermo-disinfection step.

The method provides to dispose the washing liquid at the desired temperatures in respective feed tanks hydraulically connectable to the washing chamber. Furthermore, in some forms of embodiment the method provides:

to feed a liquid for cold pre-washing by means of feed means into the chamber, and once the pre-wash is finished, to discharge the liquid used directly through the pipe;

to feed a hot liquid from a second of the tanks and to feed by means of feed means one or more chemical detergents inside the chamber and, once the hot wash with one or more chemical detergents is finished, to discharge the liquid used directly through the pipe;

to feed a liquid for hot rinsing from a third of the tanks and, once the hot wash is finished, to discharge the liquid used directly through the pipe;

to feed water, such as de-mineralized water or other liquid suitable for thermo-disinfection, by means of feed means associated with a first of the tanks, inside the chamber and, once the thermo-disinfection is finished, to accumulate the liquid used in the thermo-disinfection as a hot liquid in the third tank.

One form of embodiment of the method according to the present invention provides to re-use the hot liquid accumulated in the third tank to carry out the hot rinsing directly.

Another form of embodiment of the method according to the present invention provides to pre-heat the liquid fed by the feed means by means of heat exchange means associated with the third tank, recovering heat from the hot liquid accumulated in the third tank.

BRIEF DESCRIPTION OF THE DRAWINGS

These and other characteristics of the present invention will become apparent from the following description of a preferential form of embodiment, given as a non-restrictive example with reference to the attached drawings wherein.

To facilitate comprehension, the same reference numbers have been used, where possible, to identify identical common elements in the drawings.

DETAILED DESCRIPTION OF A PREFERENTIAL FORM OF EMBODIMENT

Figure 1:
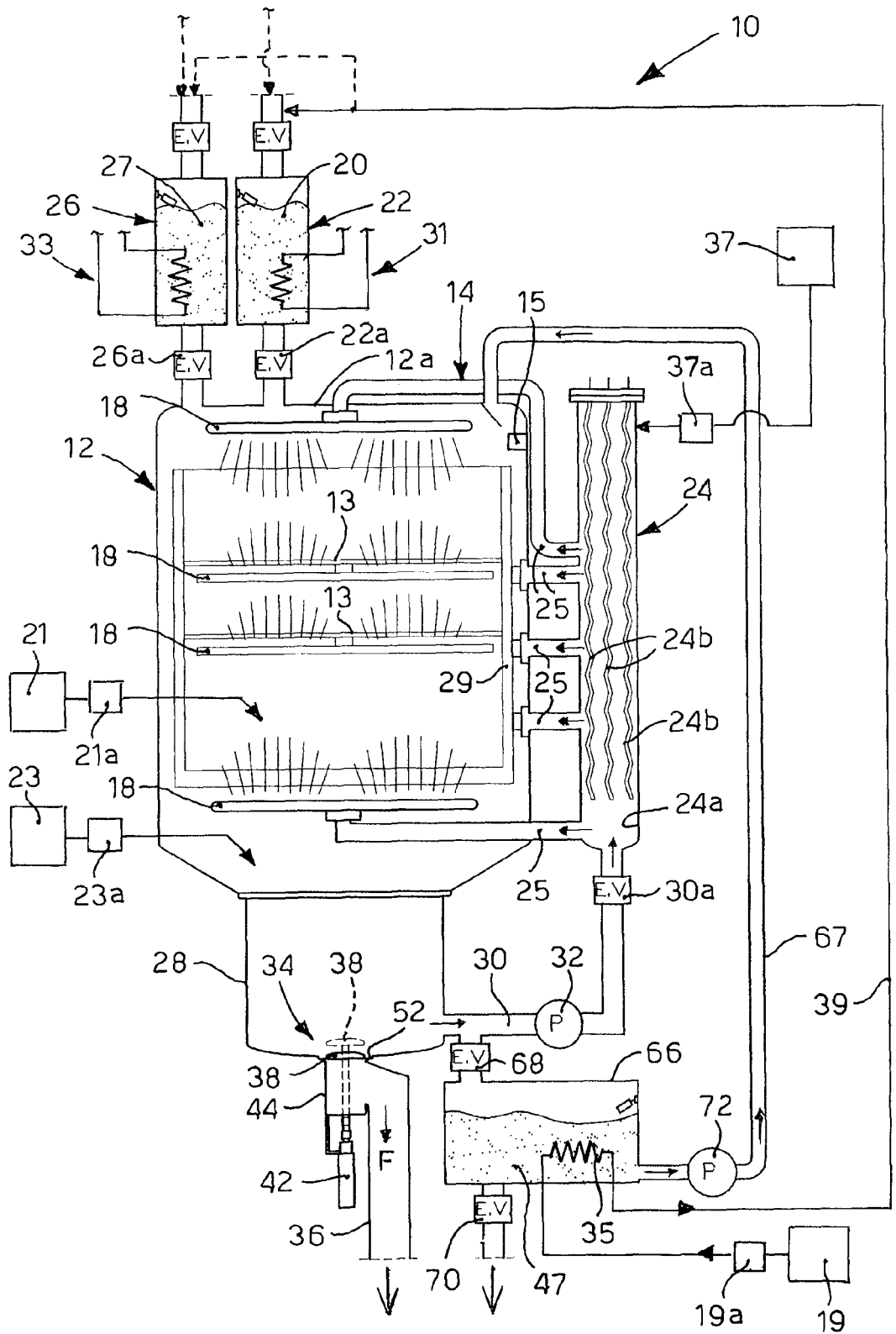
FIG. 1 is a schematic view of a washing machine according to the present invention.

With reference to FIG. 1, a washing machine 10 according to the present invention is used to perform a treatment of washing, and possible thermo-disinfection and drying of objects, such as for example objects for medical or health use, or in analysis laboratories or similar applications.

The machine 10 is used to carry out a typical cycle of washing and treating objects which provides, to give a non-restrictive example of the field of protection of the present invention:

cold pre-wash, generally with water;

washing with washing liquid, generally water, heated to between about 55° C. and about 65° C., for example 60° C., and chemical detergent;

hot rinsing;

final thermo-disinfection rinsing, at about 93-95° C. for a determinate period of time suitable to guarantee thermo-disinfection;

drying.

The machine 10 comprises a washing chamber 12 inside which the objects to be treated are disposed, possibly positioned in suitable trolleys or object-carrying baskets, on support shelves 13, positioned one above the other and distanced.

The machine 10 also comprises a hydraulic washing circuit 14 comprising a plurality of exit paths formed by nozzles mounted or made on rotors 18, or by simple holes, flat or possibly shaped, to distribute the washing liquid to the objects to be treated.

In particular, in some forms of embodiment the machine 10 comprises feed means 21 to feed the cold water inside the washing chamber 12, as indicated by arrow C, the delivery rate of which is controlled by a corresponding electrovalve 21a, to effect the cold pre-washing step.

Furthermore, in some forms of embodiment, a first tank 22 is provided, containing washing water 20, in fluidic communication with the chamber 12 by means of an electrovalve 22a, in this case disposed above the upper wall 12a of the chamber 12. The electrovalve 22a is the type that allows the rapid passage of the quantity of water from the first tank 22 to the chamber 12. The first tank 22 can be filled by connection to a water mains and/or other filling means, and can contain water 20 or other washing liquid, which can be cold or pre-heated.

The first tank 22 supplies the washing liquid water 20 at the suitable temperature for the final thermo-disinfection rinsing step, generally tending to a temperature of about 90° C.

To this purpose, the first tank 22 is associated with heat exchange or heating means 31, which heat the water 20 contained in the first tank 22 to the thermo-disinfection temperature. For example, the heat exchange or heating means 31 can consist of one or more electric resistances.

Within the washing cycle as above, in some forms of embodiment a second tank 26 is provided, in this case also disposed above the upper wall 12a of the chamber 12, selectively in communication with the inside of the chamber 12 by means of a corresponding electrovalve 26a, and containing washing liquid, typically water 27, which can be cold or pre-heated, for example coming from the water mains and/or other filling means. The electrovalve 26a is the type that allows the rapid passage of the quantity of water from the second tank 26 to the chamber 12.

The second tank 26 supplies the water for the washing step between about 55° C. and about 65° C., for example about 60° C. The water 27 is heated to the desired temperature by heat exchange or heating means 33 associated with the second tank 26. For example, the heat exchange or heating means 33 may consist of one or more electric resistances.

In order to introduce one or more chemical detergents into the chamber 12, in some forms of embodiment suitable feed means 23 are provided, associated with a pump 23a and possible flow sensors and controllers, not shown here.

Furthermore, in some forms of embodiment, feed means 19 are provided, to feed the washing liquid, advantageously demineralized water so as to reduce or eliminate the possibility of residue depositing on the objects treated; the feed means 19 feed the liquid along a circuit 39, thanks to the network pressure or by means of a pump 19a, into the first tank 22, for the purposes of thermo-disinfection.

In a variant form of embodiment, the machine 10 does not provide, or in any case does not use, the feed means 21 to feed the cold water directly inside the chamber 12, and the cold water is fed from the second tank 26, using part of the water 27 contained in the second tank 26, suitably sized to contain a volume of water necessary to carry out the two steps of pre-washing in cold water and washing at a temperature of between about 55° C. and about 65° C., for example about 60° C. In this variant, the water 27 contained in the second tank 26 is kept at a lower temperature, for example about 30° C., and subsequently, after a first determinate volume of water has been taken for the pre-wash, the quantity of water remaining is heated quickly to between about 55° C. and about 65° C., for example about 60° C., to be used in the subsequent hot washing step. In this case, the heat exchange or heating means 33 are chosen and sized to determine a rapid heating of the water needed for the hot wash while the machine 10 performs the cold pre-wash step.

In general, however, the heat exchange or heating means 31, 33 respectively associated with the first tank 22 and the second tank 26 are filled and are suitable to allow a pre-heating of the liquid inside them while the machine 10 performs the various steps of the washing cycle, in this way reducing the overall cycle times.

In this case, heating means 24 are also provided to heat the washing liquid circulating in the machine 10, so as to keep it at a desired temperature, normally between 75° C. and 95°

C., or a lower temperature, for example between 55° C. and 70° C., if a chemical wash is to be done, so as to compensate for the normal cooling of the washing liquid after it has come into contact with the object-carrying baskets or the objects to be washed themselves, which initially, or following the cold pre-wash, are at a lower temperature. The heating means 24, in one form of embodiment, are disposed outside the chamber 12. For example, the heating means 24 are rapid heating electric resistances.

Temperature sensor means 15 can be provided inside the chamber 12, which transmit an electric signal correlated to the temperature inside the chamber 12. The signal is detected by an electronic control unit, not shown, for the selective activation at least of the heating means 24, for thermostating purposes. Consequently, if the temperature inside the chamber 12 is not suitable for the determinate step in the washing cycle in progress, the heating means 24 are driven until this temperature is reached. The sensor means 15 continuously monitor the development of the temperature inside the chamber 12 so as to be able to activate the heating means 24 on each occasion for a determinate period of time.

On the bottom 28 of the chamber 12, configured as a cylinder or truncated cone or other suitable geometric solution, a first re-circling pipe 30 is provided which, by means of a first pump 32, sends the water and possible detergent mixed with it to the heating means 24. An electrovalve 30a is provided between the first pump 32 and the heating means 24 to adjust and control the stream of liquid in transit.

Furthermore, a discharge pipe 36 is provided, associated with a single rapid discharge valve 34, selectively openable, which allows to discharge directly into the sewerage system the liquid accumulated on the bottom 28. The exit of the valve 34, according to the invention, communicates directly with the inlet to the discharge valve 36. As can easily be seen in the attached drawings, the exit from the valve 34 represents, in substance, the inlet to the discharge pipe 36.

Furthermore, a recovery and accumulation tank 66 is provided for the heat exchange, which can be connected, upstream of the first pump 32, to the first pipe 30 by means of an electrovalve 68. At least part of the hot washing liquid accumulated in the tank 66, indicated by the reference number 47, is used to carry out the hot rinsing step after washing with liquid at a temperature of between about 55° C. and about 65° C., for example about 60° C., with chemical detergents and before the final thermo-disinfection rinse.

Moreover, the feed means 19 are associated along the circuit 39 that feeds the first tank 22 with heat exchange means 35, for example a coil, a bundle of tubes, a heat exchange jacket or suchlike, in which the demineralized water passes.

The tank 66 is associated with the feed means 19 of the liquid intended for thermo-disinfection, providing that the heat exchange means 35 are inserted into or associated with the tank 66 in order to recover the heat energy of the hot washing liquid 47 arriving from the chamber 12 and accumulated in the tank 66.

In this way, the demineralized water fed by the feed means 19 which flows in the heat exchange means 35 is pre-heated before it is introduced into the first tank 22, recovering part of the heat of the hot liquid 47, thus reducing the difference in temperature that the heat exchange or heating means 31 of the first tank 22 have to overcome in order to reach the thermo-disinfection temperature, and thus optimizing the overall energy consumption of the machine 12.

In the form of embodiment shown, the tank 66 is connected by means of a second re-circling pipe 67 directly with the inside of the chamber 12, in this case the second pipe 67 is directly inserted into the upper wall 12a of the chamber 12.

A second pump 72, downstream of the tank 66, provides to move at least part of the hot liquid 47 along the second pipe 67 from the tank 66 toward the entrance of the chamber 12. For the sole purposes of ordinary maintenance and cleaning, which is normally carried out once a day, it is possible to discharge the possible liquid 47 contained in the tank 66, in this case by acting on a suitable electrovalve 70.

Overall, therefore, the hydraulic circuit 14 of the machine 10 shown in FIG. 1 comprises the first pipe 30 for re-circling to the heating means 24, the second re-circling pipe 67 to recover liquid at the top of the chamber 12, the hydraulic chamber 24a of the heating means that receives the liquid from the first pipe 30, the inlet branches 25 from the hydraulic chamber 24a inside the chamber 12, the other pipes 29 that go from the branches 25 to the rotors 18, the rotors 18 themselves and the chamber 12 itself, including the bottom 28, which closes the hydraulic circuit 14.

Furthermore, the machine 10 comprises blowing means 37 to blow in a drying fluid, generally air, for the drying step. The blowing means 37 could provide, typically in series, an air pre-filter, a ventilator and a special air filter. The blowing means 37 are connected to the heating means 24 which heat the fluid to a suitable temperature for drying, from where they are then introduced into the chamber 12.

The washing method according to the present invention provides that at start-up the cold water is introduced by the feed means 23 into the chamber 12 and accumulates on the bottom 28.

Moreover, at least when the machine 10 is first started up, the tank 66 has been previously filled with heated washing liquid, in this case water, for the heat exchange and hot rinse. In this step, therefore, the electrovalve 68 remains closed.

The first pump 32 makes the cold water circulate, taking it from the bottom 28, and it is distributed, through the rotors 18, onto the objects for the cold pre-wash step and finally discharged through the discharge pipe 36, since it is dirty and contaminated water.

Subsequently, the electrovalve 26a is activated to introduce the water 27, taken to between about 55° C. and about 65° C., for example about 60° C., by the heat exchange or heating means 33, from the second tank 26 into the chamber 12, where it accumulates on the bottom 28. At the same time as the bottom 28 is filled with water 27 of the second tank 26, the feed means 23 are activated to introduce a determinate quantity of one or more chemical detergents, which are mixed with the hot water 27 on the bottom 28.

The hot water 27, mixed with the chemical detergents, is then pumped from the bottom 28 through the first pipe 30, passing along the heating means 24, which compensate for any possible cooling thereof, and is then distributed by the rotors 18 onto the objects to be treated.

The liquid is again collected on the bottom 28 and re-circled by the first pump 32, repeating the path several times for a determinate period of time, after which the liquid is discharged through the discharge pipe 36.

At this point, the hot liquid 47 accumulated in the tank 66, which at start-up of the machine 10 had previously been filled, is at least partly used for the hot rinsing step, that is, pumped by the second pump 72 along the second pipe 67, is possibly re-circled and, once this step is finished, is also discharged through the discharge pipe 36.

For the final thermo-disinfection rinsing step, the water 20 in the first tank 22 is used, which comes from the feed means 19, which has been pre-heated by the hot liquid 47 passing in the heat exchange means 35 through the tank 66, and has also been heated by the heating means 31 to the temperature suitable for thermo-disinfection.

In particular, by activating the electrovalve 22*a*, the water 22 is introduced into the chamber 12, accumulates on the bottom 28 and is pumped into the heating means 24 which take it to, or keep it at, the thermo-disinfection temperature.

From here, the thermo-disinfection water 20 is introduced into the rotors 18 and hits the objects to be treated. In particular, until the temperature sensor means 15 signal that the desired thermo-disinfection temperature has been reached inside the chamber 22, the water 20 is continuously re-circled by the first pump 32 from the bottom 28 to the heating means 24 and from here to the rotors 18.

Once the desired temperature has been reached, the water 20 continues to be re-circled in the machine 10 and the period of time, for example about 1-10 minutes, dedicated to thermo-disinfection begins.

At the end of this period, the water 20, which is substantially clean and which has a high heat content, is not discharged through the discharge pipe 36 but, by activating the electrovalve 68, is advantageously accumulated in the tank 66, so as to give up at least part of its heat, by means of the heat exchange or heating means 35, to the demineralized water arriving from the feed means 19, as described above, for pre-heating purposes. The demineralized water accumulated in the tank 66 is used directly, as explained above, for the hot rinsing step before the final thermo-disinfection.

Finally, the drying step is carried out, providing to close the electrovalves 30*a* and 68 and activating instead the electrovalve 37*a*, which allows to introduce drying fluid into the heating means 24 and from here into the chamber 12, to dry the thermo-disinfected objects.

In some forms of embodiment, the heating means 24 in this case comprise a hydraulic chamber or collector 24*a*, outside the chamber 12, in which the washing liquid and possibly the drying fluid pass, and heating elements 24*b*, advantageously rapid heating, such as electric heating members or heat exchangers with heat-carrying fluid or other, housed in the hydraulic chamber 24*a*. The hydraulic chamber 24*a* is hydraulically connected on one side to the inside of the chamber 12 and on the other side to the first re-circling pipe 30, as well as to the blowing means 37, as we said.

In particular, the heating means 24 are connected downstream, along the path of the liquid, with other branches 25 of the hydraulic circuit 14 which, in turn, enter into the washing chamber 12 in other pipes 29 of the circuit, toward the rotors 18, in order to spray the heated liquid onto the objects to be washed.

As mentioned above, for drying purposes the machine 10 advantageously provides that the same hydraulic circuit 14 is used, at least in some of its essential parts, for the transit, heating and blowing of the drying air arriving from the blowing means 37.

In particular, the drying air can be introduced, generally by a pressing ventilation, from a suitable entrance into the hydraulic circuit 14, shown in this case in correspondence with the heating means 24, and blown onto the washed objects to be dried, for example by means of the same exits for the liquid provided on the rotors 18. In this form of embodiment, the air inlet may be directly connected to the hydraulic chamber 24*a* of the heating means 24, where the air is heated to the temperature needed for drying by the heating elements 24*b* that heat the washing liquid, and from here pass through the branches 25 and other pipes 29, to the objects to be dried in the chamber 12.

In some forms of embodiment, for discharge through the discharge pipe 36, the machine 10 provides a discharge aperture 52 made on the bottom 28, in this case circular; at exit from the discharge aperture 52 the discharge valve 34 is directly mounted (FIGS. 1 and 2), which as we said is in turn directly connected to the entrance of the discharge pipe 36 which discharges directly into the sewerage system provided for the purpose, without requiring other intermediate hydraulic members, pipes or tanks, as indicated by arrow F.

According to some forms of embodiment of the present invention, the rapid discharge valve 34 is configured to allow a rapid discharge delivery rate comprised between 25 l/min and 200 l/min, preferably between 100 l/min and 150 l/min.

Figure 2:
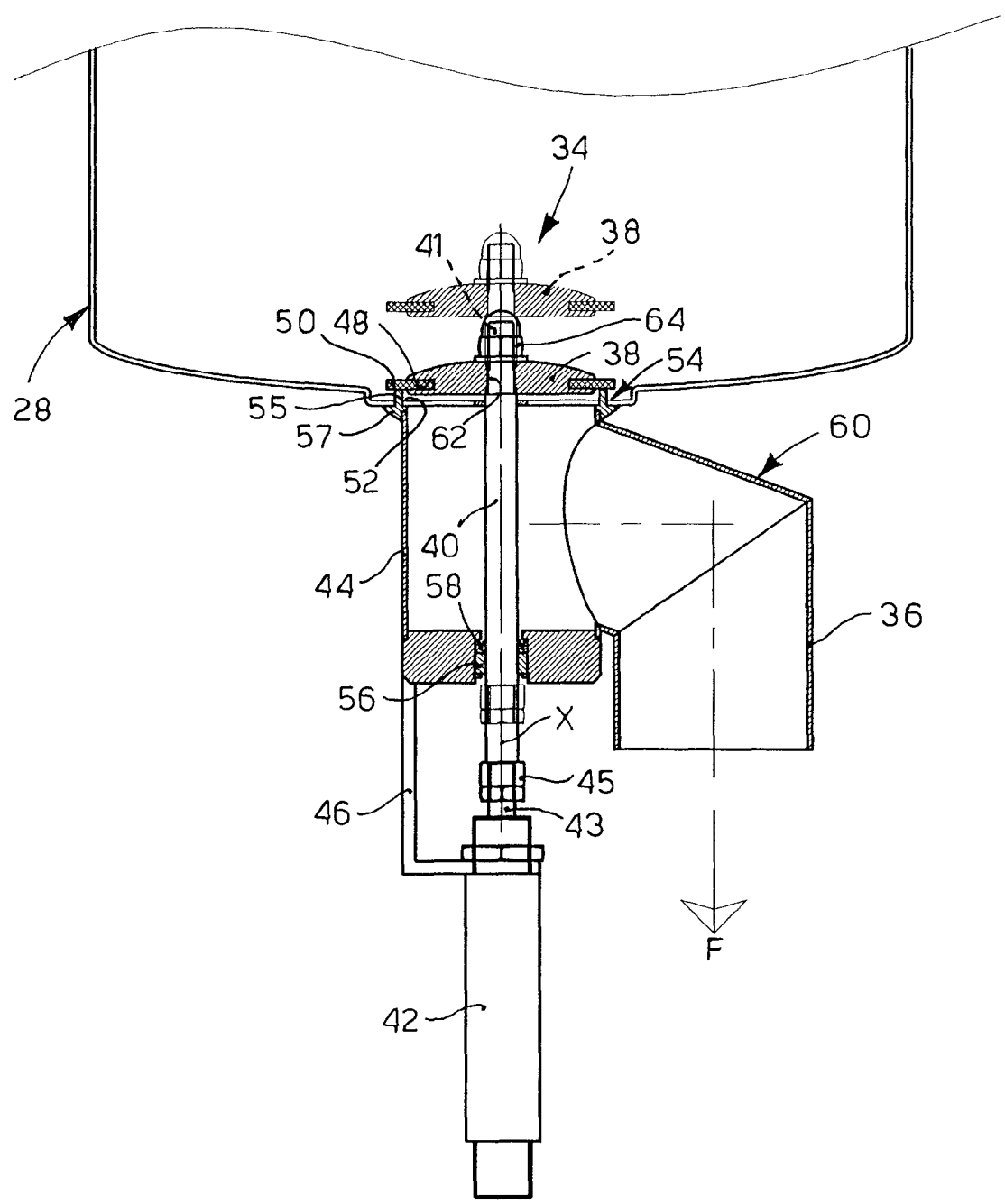
FIG. 2 is an enlarged detail of a detail of FIG. 1.

In the case shown here, the valve 34 is provided with a shut-off plate 38, mating in shape, in this case circular, with the discharge aperture 52 and positioned mobile along a determinate movement axis X (FIG. 2), inside the bottom 28 of the chamber 12 between a first lowered position in which it closes the aperture 52, shown by continuous lines in FIGS. 1 and 2, and a second raised position, distanced from the aperture 52, shown by dashes in FIGS. 1 and 2, to allow the rapid passage of the washing liquid to be discharged.

The valve 34 comprises rapid drive mechanical means, in this case formed by an axial drive rod 40, mobile with an alternate motion along the axis X, to determine a rapid displacement of the plate 38 between the first and second position, associated with a linear actuator 42 directly connected to the rapid drive mechanical means, in this case to the rod 40. The linear actuator 42 determines the alternate axial movement of the rod 40, and hence the rapid passage of the plate 38 between the open and closed position.

Providing a plate 38 with a wider shape and reduced thickness, substantially disc-shaped, facilitates the rapid displacement thereof by the rod 40 driven by the linear actuator 42.

In the solution shown here, given as a non-restrictive example of the field of protection, an elbow connection 60 is provided between the aperture 52 and the discharge pipe 36.

The elbow connection 60 has a tubular portion 44, directly connected to the aperture 52 and substantially coaxial with the axis X, inside which the movement is provided of the rod 40 along the axis X.

The rod 40 has a threaded end 41 which is inserted through a hole 62 into the plate 38, and then cooperates with a nut 64 for clamping. An opposite end 43 of the rod 40 is instead constrained to the linear actuator 42 by means of a nut 45. The linear actuator 42 is in turn suspended from the tubular portion 44 of the elbow connection 60 by means of a bracket 46.

The bottom of the tubular portion 44 is holed, for the insertion and sliding of the rod 40, providing a suitable mouth 56 to facilitate the movement of the rod 40, and a hydraulic seal element 58.

The plate 38 has a continuous groove 48 on its periphery, in this case circular, in which a hydraulic seal element 50 is disposed, in this case an annular packing, generally made of deformable plastic material, so as to achieve the hydraulic seal. The hydraulic seal element 50 protrudes beyond the peripheral bulk of the plate 38 by a determinate amount, to cooperate directly or indirectly with the aperture 52 and to achieve the hydraulic seal.

In this case, a positioning element 54, in this case configured as a ring, is disposed as a collar around the aperture 52, coupling through geometric interference. The positioning element 54 provides a ridge 55, in this case annular, which protrudes inside the chamber 12, and on which the hydraulic seal element 50 abuts, in particular the part protruding beyond the plate 38, and an undercut tooth 57, also in this case annular, for the axial clamping.

The invention claimed is:

1. A washing machine to effect a washing treatment, thermo-disinfection and optional drying of objects, comprising:
   a washing chamber for disposing therein the objects to be treated, wherein the washing chamber comprises a bottom, having on the bottom a corresponding discharge aperture on which, at exit, a single valve for the discharge of a washing liquid is directly mounted, an exit of said valve is in turn connected in direct communication to an inlet of a pipe for discharging directly into a sewerage system;
   a washing circuit comprising:
      a plurality of washing liquid distributors providing exit paths for distributing the washing liquid toward the objects to be treated, the washing liquid distributors comprising nozzles or holes for passing the washing liquid therethrough;
      washing liquid feeder conduits to feed the respective distributors,
      a washing liquid heater for heating the washing liquid to a desired temperature prior to feeding the washing liquid feeder conduits which in turn feed the washing liquid to the distributors which discharge the washing liquid into the washing chamber, wherein the washing liquid heater is disposed outside the washing chamber,
   wherein the washing circuit comprises a first re-circling circuit comprising a first re-circling conduit in communication with the bottom of the washing chamber and the washing liquid heater for passing the washing liquid from the bottom of the washing chamber to the washing liquid heater, the first re-circling conduit comprising a pump to pump the washing liquid toward the washing liquid heater to be reintroduced into the washing chamber;
   an electrovalve mounted on the first re-circling conduit between the pump and the washing liquid heater, to adjust and to control a first stream of washing liquid in transit; and
   a temperature sensor disposed inside the washing chamber for transmitting an electric signal to an electronic control unit, the electrical signal correlated to a temperature inside the washing chamber for selective activation of the washing liquid heater,
   a blower for blowing in a drying fluid at a temperature inside the washing chamber for a drying step, the blower connected to the washing liquid heater to heat the drying fluid to a temperature for drying the washed objects, the washing liquid heater in fluid communication with the washing chamber to pass the heated drying fluid into the washing chamber,
   wherein the washing circuit comprises a recovery and accumulation tank, to receive and accumulate a determinate quantity of hot washing liquid from the bottom of the chamber, and a second re-circling circuit comprising a second re-circling conduit having a first end and a second end,
   wherein the first end is connected to the recovery and accumulation tank and the second end terminates into an upper portion of the washing chamber for transferring at least a portion of the quantity of the hot washing liquid present in the recovery and accumulation tank to directly inside the upper portion of the washing chamber,
   further comprising a first thermo-disinfection liquid tank for supplying, through a top wall of the washing chamber, a second stream of the washing liquid at a temperature for a final thermo-disinfection rinsing,
   further comprising a first feeder adapted to feed cold water, or other pre-wash liquid, into the chamber, a second feeder adapted to feed one or more chemical detergent components inside the chamber; and a third feeder, associated with the first thermo-disinfection liquid tank, and adapted to feed water, or other liquid for thermo-disinfection, into the chamber, and
   further comprising a heat exchanger located within the recovery and accumulation tank, the third feeder in fluid communication with an inlet of the heat exchanger, a discharge conduit in fluid communication with an outlet of the heat exchanger, the heat exchanger configured to pre-heat liquid fed by the third feeder and to recover heat from hot liquid accumulated in the recovery and accumulation tank and then pass the pre-heated liquid feed through the discharge conduit to the first thermo-disinfection liquid tank.

2. The washing machine as in claim 1, wherein the valve for the discharge of the washing liquid has a cut-off plate with a shape mating to the discharge aperture and positioned to be mobile mobile inside the bottom of the washing chamber between a first position in which the cut-off plate closes said discharge aperture and a second position in which the cut-off plate is distanced from said discharge aperture to allow the passage of the washing liquid to be discharged, said valve comprising a mechanical drive configured to determine a displacement of the cut-off plate between the first and second position and associated with an actuator directly connected to said mechanical drive.

3. The washing machine as in claim 2, wherein said mechanical drive comprises a drive rod connected to the cut-off plate, which extends linearly from the plate toward the outside with respect to the discharge aperture and connected at the lower part to said actuator.

4. The washing machine as in claim 2, wherein said mechanical drive comprises a rocker arm.

5. The washing machine as in claim 1, further comprising a first heater associated with the first thermo-disinfection liquid tank and configured to heat liquid to a temperature for thermo-disinfection.

6. The washing machine as in claim 1, further comprising a second heater associated with a second thermo-disinfection liquid tank and configured to heat liquid to a temperature between 55° C. and 65° C.

7. The washing machine as in claim 1, wherein said second re-circling conduit is configured to transfer said at least a portion of the quantity of hot washing liquid present in the recovery and accumulation tank, directly inside the washing chamber through a top wall of the washing chamber.

8. The washing machine as in claim 1, wherein the drying fluid comprises drying air,
   wherein the blower is in fluid communication with the washing liquid heater to discharge the drying air into the washing liquid heater, wherein the washing liquid heater is a heater to heat the drying air to the temperature for drying the washed objects, such that the washing liquid heater is configured to heat the washing liquid or the drying air and respectively then discharge the washing liquid or the drying air from the washing liquid heater into the washing chamber.

9. The washing machine as in claim 1, wherein the washing liquid comprises water.

10. The washing machine as in claim 1, wherein the water comprises de-mineralized water.

11. The washing machine as in claim 1, wherein the washing liquid heater comprises a hydraulic chamber and heating elements housed in the hydraulic chamber.

12. The washing machine as in claim 11, wherein the hydraulic chamber is hydraulically connected on one side to the inside of the washing chamber and on an other side to the first re-circling conduit of the first re-circling circuit.

13. The washing machine as in claim 1, wherein the temperature sensor is configured to continuously monitor development of the temperature inside the washing chamber to selectively activate the washing liquid heater on each occasion for a determinate period of time.

14. The washing machine as in claim 13, wherein the temperature sensor is configured to selectively activate the washing liquid heater such that if the temperature inside the washing chamber is too low for a determinate step in the washing cycle in progress, the washing liquid heater is driven.

15. The washing machine as in claim 1, wherein the washing liquid heater comprises electric resistances.

16. The washing machine as in claim 1,
wherein the first re-circling conduit comprises a first pipe having an inlet connected to the bottom of the washing chamber and an outlet connected to the pump;
wherein the recovery and accumulation tank is connected upstream of the pump to the first pipe by an electrovalve, the recovery and accumulation tank is connected by the second re-circling conduit with the inside of the washing chamber.

17. The washing machine as in claim 16, wherein the recovery and accumulation tank, comprises a bottom, having on the bottom a corresponding discharge aperture on which, at exit, a single valve for the discharge of the washing liquid is directly mounted, the exit of said valve is in turn connected in direct communication to an inlet of a second pipe for discharging directly into a sewerage system.

18. A washing machine to effect a washing treatment, thermo-disinfection and optional drying of objects, comprising:
a washing chamber for disposing therein the objects to be treated, wherein the washing chamber comprises a bottom, having on the bottom a corresponding discharge aperture on which, at exit, a single valve for the discharge of a washing liquid is directly mounted, an exit of said valve is in turn connected in direct communication to an inlet of a pipe for discharging directly into a sewerage system;
a washing circuit comprising:
a plurality of washing liquid distributors providing exit paths for distributing the washing liquid toward the objects to be treated, the washing liquid distributors comprising nozzles or holes for passing the washing liquid therethrough;
washing liquid feeder conduits to feed the respective distributors,
a washing liquid heater for heating the washing liquid to a desired temperature prior to feeding the washing liquid feeder conduits which in turn feed the washing liquid the to distributors which discharge the washing liquid into the washing chamber, wherein the washing liquid heater is disposed outside the washing chamber,
wherein the washing circuit comprises a first re-circling circuit comprising a first re-circling conduit in communication with the bottom of the washing chamber and the washing liquid heater for passing the washing liquid from the bottom of the washing chamber to the washing liquid heater, the first re-circling conduit comprising a pump to pump the washing liquid toward the washing liquid heater to be reintroduced into the washing chamber;
an electrovalve mounted on the first re-circling conduit between the pump and the washing liquid heater, to adjust and to control a first stream of washing liquid in transit; and
a temperature sensor disposed inside the washing chamber for transmitting an electric signal to an electronic control unit, the electrical signal correlated to a temperature inside the washing chamber for selective activation of the washing liquid heater,
a blower for blowing in a drying fluid at a temperature inside the washing chamber for a drying step, the blower connected to the washing liquid heater to heat the drying fluid to a temperature for drying the washed objects, the washing liquid heater in fluid communication with the washing chamber to pass the heated drying fluid into the washing chamber,
wherein the washing circuit comprises a recovery and accumulation tank, to receive and accumulate a determinate quantity of hot washing liquid from the bottom of the chamber, and a second re-circling circuit comprising a second re-circling conduit having a first end and a second end,
wherein the first end is connected to the recovery and accumulation tank and the second end terminates into an upper portion of the washing chamber for transferring at least a portion of the quantity of the hot washing liquid present in the recovery and accumulation tank to directly inside the upper portion of the washing chamber,
wherein the first re-circling conduit comprises a first pipe having an inlet connected to the bottom of the washing chamber and an outlet connected to the pump;
wherein the recovery and accumulation tank is connected upstream of the pump to the first pipe by an electrovalve, the recovery and accumulation tank is connected by the second re-circling conduit with the inside of the washing chamber,
further comprising a first thermo-disinfection liquid tank for supplying, through a top wall of the washing chamber, a second stream of the washing liquid at a temperature for a final thermo-disinfection rinsing step,
further comprising a conduit for feeding liquid for thermo-disinfection to an inlet of a heat exchanger within the recovery and accumulation tank to recover heat energy of the hot washing liquid from the washing chamber within the recovery and accumulation tank and for passing the liquid for thermo-disinfection from an outlet of the heat exchanger to the first thermo-disinfection liquid tank.

* * * * *